(12) United States Patent
Sprenger et al.

(10) Patent No.: US 10,716,321 B2
(45) Date of Patent: Jul. 21, 2020

(54) OLIGOSACCHARIDE MIXTURE AND FOOD PRODUCT COMPRISING SAME

(71) Applicant: NESTEC S.A., Vevey (CH)

(72) Inventors: Norbert Sprenger, Savigny (CH); Jean-Richard Neeser, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 120 days.

(21) Appl. No.: 15/838,551

(22) Filed: Dec. 12, 2017

(65) Prior Publication Data

US 2018/0110253 A1    Apr. 26, 2018

Related U.S. Application Data

(62) Division of application No. 13/988,984, filed as application No. PCT/EP2011/070566 on Nov. 21, 2011, now Pat. No. 9,854,826.

(30) Foreign Application Priority Data

Nov. 23, 2010  (EP) .................................... 10192231

(51) Int. Cl.
*A61K 31/702* (2006.01)
*A23L 33/10* (2016.01)
*A61K 45/06* (2006.01)
*A23L 33/00* (2016.01)
*A23L 33/21* (2016.01)

(52) U.S. Cl.
CPC .............. *A23L 33/10* (2016.08); *A23L 33/21* (2016.08); *A23L 33/40* (2016.08); *A61K 31/702* (2013.01); *A61K 45/06* (2013.01); *A23V 2002/00* (2013.01); *A23V 2200/3202* (2013.01)

(58) Field of Classification Search
None
See application file for complete search history.

(56) References Cited

U.S. PATENT DOCUMENTS

| 6,146,670 | A | 11/2000 | Prieto et al. |
| 6,946,451 | B2 | 9/2005 | Takada et al. |
| 8,771,674 | B2 | 7/2014 | Sprenger |
| 2003/0181401 | A1 | 9/2003 | Takada et al. |
| 2004/0013787 | A1* | 1/2004 | Theuer ................... A23D 7/003 426/601 |
| 2007/0275881 | A1 | 11/2007 | Morrow et al. |
| 2009/0197806 | A1 | 8/2009 | Morrow et al. |

(Continued)

FOREIGN PATENT DOCUMENTS

| JP | 2003292444 | 10/2003 |
| WO | 2009151315 | 12/2009 |

OTHER PUBLICATIONS

Thurl et al., "Variations of neutral oligosaccharides and lactose in human milk during the feeding." Zeitschrift für Emaährungswissenschaft 32.4 (1993) pp. 262-269. XP002071967.

(Continued)

*Primary Examiner* — Felicia C Turner
(74) *Attorney, Agent, or Firm* — K&L Gates LLP (57) ABSTRACT

Oligosaccharide mixtures consisting of at least one N-acetyl-lactosamine, at least one sialylated oligosaccharide, and at least one fucosylated oligosaccharide are provided. Food products, especially infant formula, comprising the oligosaccharide mixture are also provided.

7 Claims, 4 Drawing Sheets

Experimental results showing metabolic stimulation of a bifidobacterium (B. longum subsp infantis) in DMEM culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL. (n=6; mean with SEM are shown; significance by ANOVA indicated (p<0.01).
Note: Only the blend of LNnT, 6SL and 2FL stimulated significantly the production of acetate.

(56) References Cited

U.S. PATENT DOCUMENTS

| | | |
|---|---|---|
| 2009/0263537 A1 | 10/2009 | Schmitt et al. |
| 2009/0305996 A1 | 12/2009 | Beermann et al. |
| 2010/0105615 A1 | 4/2010 | Rosales et al. |
| 2010/0278781 A1 | 11/2010 | Hougee et al. |

OTHER PUBLICATIONS

Thurl et al., "Quantification of individual oligosaccharide compounds from human milk using high-pH anion-exchange chromatography," Analytical Biochemistry 235.2 (1996) pp. 202-206. XP002439151.

Russia Office Action for Application No. 2013128595/13(042596), dated Dec. 10, 2015, 8 pages.

\* cited by examiner

*Figure 1.* Experimental results showing metabolic stimulation of a bifidobacterium (B. longum subsp infantis) in DMEM culture medium either without additional carbohydrates or with additional glucose (Glc), or lacto-N-neotetraose (LNnT) or 2'fucosyllactose (2FL) or 6'sialyllactose (6SL) or a blend of LNnT, 6SL and 2FL. (n=6; mean with SEM are shown; significance by ANOVA indicated ($p<0.01$).

Note: Only the blend of LNnT, 6SL and 2FL stimulated significantly the production of acetate.

Figure 2. Experimental results showing in vitro growth of a bifidobacterium (B. longum subsp infantis) in culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL.. (n=4; mean with SEM are shown; significance by ANOVA ($p<0.02$) indicated by small letters).

*Figure 3.* Experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk. Here the represented oligosaccharide blend is the sum of 2'fucosyllactose (2FL), Lacto-N-neotetraose (LNnT) and 6'siayllactose (6SL). (Statistical significance is indicated)

*Figure 4. Experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk. Here the represented oligosaccharide blend is the sum of 2'fucosyllactose (2FL), Lacto-N-neotetraose (LNnT), Lacto-N-tetraose (LNT), 6'sialyllactose (6SL) and 3'siayllactose (3SL). (Statistical significance is indicated)*

OLIGOSACCHARIDE MIXTURE AND FOOD PRODUCT COMPRISING SAME

CROSS REFERENCE TO RELATED APPLICATIONS

The present application is a divisional application of U.S. patent application Ser. No. 13/988,984, filed on May 22, 2013, which is a National Stage of International Application No. PCT/EP2011/070566, filed on Nov. 21, 2011, which claims priority to European Patent Application No. 10192231.8, filed Nov. 23, 2010, the entire contents of each of which are being incorporated herein by reference.

FIELD OF THE INVENTION

The invention relates to an oligosaccharide mixture and to a food product comprising the oligosaccharide mixture, especially infant formula.

BACKGROUND

The human colon is colonized by a wide range of bacteria having both positive and negative effects on the gut's physiology, as well as having other systemic influences. The predominant groups of bacteria found in the colon include *Bacteroides* species, in particular *Bifidobacteria, Eubacteria, Clostridia* and *Lactobacilli*. These bacteria have fluctuating activities in response to substrate availability, redox potential, pH, $O_2$ tension and their distribution in the colon. In general intestinal bacteria can be divided into species exerting either potentially harmful or beneficial effects on their host. Pathogenic effects (which may be caused by *Clostridia* or *Bacteroides*, for example) include diarrhea, infections, liver damage, carcinogenesis and intestinal putrefaction. Health-promoting effects may be induced through the inhibition of the growth of harmful bacteria, the stimulation of immune functions, improvements in the digestion and absorption of essential nutrients and the synthesis of vitamins. An increase in the numbers and/or activities of bacterial groups (such as *Bifidobacteria* and *Lactobacilli*) that may have health promoting properties is desirable.

Concerning the specific case of infants, immediately before birth, the gastrointestinal tract of an infant is thought to be sterile. During the process of birth, it encounters bacteria from the digestive tract and skin of the mother and starts to become colonized. Large differences exist with respect to the composition of the gut microbiota in response to the infant's feeding. The fecal flora of breast-fed infants includes appreciable populations of *bifidobacteria* with some *Lactobacillus* species, whereas formula-fed infants have more complex microbiota, with *Bifidobacteria* species and *Bacteroides* species, *Clostridia* and Streptococci being usually present. After weaning, a pattern of gut microbiota resembling that of an adult pattern becomes established.

Mother's milk is recommended for all infants. However, in some cases breastfeeding is inadequate or unsuccessful for medical reasons or because of mother choice not to breast-feed. Infant formulae have been developed for these situations.

One approach to promote the numbers and/or activities of beneficial bacteria in the colon is the addition of prebiotics to foodstuffs. A prebiotic is a non-digestible food ingredient that beneficially affects the host by selectively stimulating the growth and/or activity of one or a limited number of bacteria in the colon, thereby improving the host's health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS).

Human milk is known to contain a larger amount of indigestible oligosaccharides than most other animal milks. In fact, indigestible oligosaccharides represent the third largest solid component (after lactose and lipids) in breast milk, occurring at a concentration of 12-15 g/l in colostrum and 5-8 g/l in mature milk. Human milk oligosaccharides are highly resistant to enzymatic hydrolysis, indicating that these oligosaccharides may display essential functions not directly related to their caloric value.

As the understanding of the composition of human milk improves, it has also been proposed to add prebiotics to infant formula. Various infant formulae supplemented with prebiotics such as mixtures of fructooligosaccharides and galactooligosaccharides, for example, are commercially available. However, such mixtures provide only an approximation to the mixture of oligosaccharides present in human milk. Over 100 different oligosaccharide components have been detected in human milk, some of which have not yet been detected, or have been detected only in small quantities, in animal milks such as bovine milk. Some sialylated oligosaccharides and fucosylated oligosaccharides are present both in bovine milk and in colostrum, but only in very small quantities.

EP 0 975 235 B1 from Abbott Laboratories describes a synthetic nutritional composition comprising one or more human milk oligosaccharides, wherein the HMOs in the composition are chosen among a group of eight HMOs (3-fucosyllactose, lacto-N-fucopentaose III, lacto-N-fucopentaose II, difucosyllactose, 2'-fucosyllactose, lacto-N-fucopentaose I, lacto-N-neotetraose and lacto-N-fucopentaose V) wherein the composition is intended for cases of normal, healthy infants, children, adults or subjects having specialized needs such as those that accompany certain pathological conditions. This European patent states that, generally speaking, oligosaccharides protect infants from viral and bacterial infections of the respiratory, gastrointestinal and uro-genital tracts.

An object of the present invention is to provide a food product which is effective as a prebiotic, particularly in the human gut.

There is a need for a food product, especially targeted at babies, infants and/or new born infants that help securing a normal immune or inflammation status or mitigate or reduce the effect of food allergies.

There is a need for a food product that provides the above benefits while preserving a balanced normal metabolism in the individual.

There is a need for an improvement of human gut conditions, by a non-drug-based intervention that is compatible with fragile individuals like infants or babies.

There is a need for a food product that provides an oral tolerance to allergens.

SUMMARY

The present invention provides an oligosaccharide mixture comprising at least one N-acetyl-lactosamine, at least one sialylated oligosaccharide and at least one fucosylated oligosaccharide.

The above mixture of ingredients is a new protective and immuno-modulating composition that is particularly effective as a prebiotic in a food product. The mixture is structurally closer to human breast milk oligosaccharides than commercially available prebiotic ingredients, such as FOS and GOS, due to the fact it comprises, for example, a mixture of specific acidic (sialylated) and neutral (fucosylated or N-acetyl-lactosamine) oligosaccharides.

In one embodiment, the oligosaccharide mixture may be derived from animal milk, such as one or more of cow, goat or buffalo milk.

In another embodiment, the oligosaccharide mixture is a synthetic composition.

In another aspect the invention relates to a food product comprising an oligosaccharide mixture as described above. Optionally the food product is proposed as infant food or formula, but the product may be used in any food or drink consumed by babies, infants or adults. Adults usually use the oligosaccharide mixture according to the invention when needed, in particular in the technical field of clinical nutrition. Consumption of a food product containing such an oligosaccharide mixture as a prebiotic will selectively promote the growth and/or activity of one or a limited number of beneficial bacteria in the colon, and will thus improve the host's health.

DETAILED DESCRIPTION

As used herein, the following terms have the following meanings.

The term "infant" means a child under the age of 12 months.

The term "young child" means a child aged between one and three years.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The term "follow-on formula" means a foodstuff intended for particular nutritional use by infants aged over four months and constituting the principal liquid element in the progressively diversified diet of this category of person.

The term "starter infant formula" means a foodstuff intended for particular nutritional use by infants during the first four months of life.

The term "baby food" means a foodstuff intended for particular nutritional use by infants during the first years of life.

The term "infant cereal composition" means a foodstuff intended for particular nutritional use by infants during the first years of life.

The term "growing-up milk" means a milk-based beverage adapted for the specific nutritional needs of young children.

The term "enhancement of the oral tolerance to allergens" means the reduction of the sensibility to allergens when taken orally.

The term "nutritional composition" means a composition which nourishes a subject. This nutritional composition is usually to be taken orally or intravenously, and it usually includes a lipid or fat source and a protein source.

The term "synthetic composition" means a composition obtained by chemical and/or biological (e.g. enzymes) means, which can be chemically identical to the mixture naturally occurring in mammalian milks. A composition is said to be synthetic as soon as at least one of its components is obtained by chemical and/or biological (e.g. enzymatic) means.

The term "hypoallergenic composition" means a composition which is unlikely to cause allergic reactions.

The term "sialylated oligosaccharide" means an oligosaccharide having a sialic acid residue.

The term "fucosylated oligosaccharide" means an oligosaccharide having a fucose residue.

The term "prebiotic" means non-digestible carbohydrates that beneficially affect the host by selectively stimulating the growth and/or the activity of healthy bacteria such as *bifidobacteria* in the colon of humans (Gibson G R, Roberfroid M B. *Dietary modulation of the human colonic microbiota: introducing the concept of probiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10).

An "allergy" is an allergy which has been detected by a medical doctor and which can be treated occasionally or in a more durable manner A "food allergy" is an allergy with respect to a nutritional composition.

All percentages are by weight unless otherwise stated.

The oligosaccharide mixture according to the invention is preferably a hypoallergenic composition.

The invention provides an oligosaccharide mixture which comprises at least one N-acetyl-lactosamine selected from the group comprising lacto-N-tetraose and lacto-N-neotetraose, at least one sialylated oligosaccharide selected from the group comprising 3'-sialyllactose and 6'-sialyllactose, and at least one fucosylated oligosaccharide selected from the group comprising 2'-fucosyllactose, 3-fucosullactose, difucosyllactose, lacto-N-fucopentaoses (that is to say lacto-N-fucopentaose I, lacto-N-fucopentaose II, lacto-N-fucopentaose III, and lacto-N-fucopentaose V), lacto-N-difucohexaose I, monofucosyllacto-N-hexaose, Difucosyllacto-N-hexaose I and Difucosyllacto-N-neohexaose II.

The inventors have discovered that, surprisingly, the oligosaccharide mixture according to the invention, when comprised in a food product, is particularly advantageous for preventing and reducing the risk and/or reducing the severity and/or reducing the occurrence of food allergies and related food allergy effects on health. Said effects are preferably (i) skin effects, atopic dermatitis, rash, or redness; (ii) effects on the immune system or inflammation status; or (iii) effects on the gastro-intestinal system such as colics, abdominal pain and the like.

The oligosaccharide mixture of the invention may be derived from animal milks. The milk may be obtained from any mammal, in particular from cows, goats, buffalos, horses, elephants, camels or sheep.

The oligosaccharide mixture contains at least one N-acetyl-lactosamine That is to say that it contains N-acetyl-lactosamine and/or an oligosaccharide containing N-acetyl-lactosamine. Suitable oligosaccharides containing N-acetyl-lactosamine include lacto-N-tetraose (LNT) and lacto-N-neotetraose (LNnT).

Thus, according to the invention, the N-acetyl-lactosamine is preferably selected from the group comprising lacto-N-tetraose (LNT) and lacto-N-neotetraose (LNnT).

LNT and LNnT may be synthesized chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetyl-hexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

Preferably the oligosaccharide mixture according to the invention contains from 0.1 to 3 g N-acetyl-lactosamine lactose(s)/100 g oligosaccharide mixture on a dry weight basis.

The sialylated oligosaccharides 3'-sialyllactose and 6'-sialyllactose may be isolated by chromatography or filtration from a natural source such as animal milks. Alternatively, they may also be produced by biotechnological means using specific sialyltransferases or sialidases, neuraminidases, either by an enzyme based fermentation technology (recombinant or natural enzymes), by chemical synthesis or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerization (DP), from DP=1 onwards.

Preferably the oligosaccharide mixture according to the invention contains from 0.05 to 2 g, more preferably 0.1 to 2 g, of sialylated oligosaccharide(s) per 100 g of oligosaccharide mixture on a dry weight basis.

The fucosylated oligosaccharide may be selected from the group comprising 2'-fucosyllactose, 3-fucosyllactose, difucosyllactose, lacto-N-fucopentaose I, lacto-N-fucopentaose II, lacto-N-fucopentaose III, lacto-N-fucopentaose V, lacto-N-difucohexaose I, monofucosyllacto-N-hexaose, Difucosyllacto-N-hexaose I and Difucosyllacto-N-neohexaose II.

A particularly preferred fucosylated oligosaccharide is 2'-fucosyllactose.

The fucosylated oligosaccharide may be isolated by chromatography or filtration technology from a natural source such as animal milks. Alternatively, it may be produced by biotechnological means using specific fucosyltransferases and/or fucosidase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

Preferably, the oligosaccharide mixture according to the invention contains from 0.1 to 3 g of fucosylated oligosaccharide(s) per 100 g of oligosaccharide mixture on a dry weight basis.

In a preferred embodiment, the oligosaccharide mixture of the invention comprises from 0.05 to 3 g of the total amount of N-acetyl-lactosamine(s), sialylated oligosaccharide(s) and fucosylated oligosaccharide(s) per 100 g of oligosaccharide mixture.

In a preferred aspect of the invention, the oligosaccharide mixture described above is incorporated into a food product. In the context of the present invention, the term "food product" is intended to encompass any consumable substance. Hence, it may be a product intended for consumption by humans, in particular an infant formula, a follow-up formula, infant or young children food such as infant cereals, and the like. In particular, the oligosaccharide mixtures of the invention can be incorporated into infant formulas, dehydrated milk or cereal mixtures.

Thus the invention also includes a food product comprising the oligosaccharide mixture of the invention. The food product preferably comprises a protein source, a fat source and a carbohydrate source.

The food product according to the invention is preferably a hypoallergenic composition.

The food product according to the invention also contains a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. However, the protein source preferably comprises between 20% and 95% of whey proteins and/or proteins derived from whey. As far as whey proteins are concerned, the protein source may be based on acid whey or sweet whey or mixtures thereof and may include alpha-lactalbumin and beta-lactoglobulin in any desired proportions.

The food product according to the present invention generally contains a carbohydrate source. This is particularly preferable in the case where the food product of the invention is an infant formula. In this case, any carbohydrate source conventionally found in infant formulae such as lactose, saccharose, maltodextrin, starch and mixtures thereof may be used although the preferred source of carbohydrates is lactose.

The food product according to the present invention generally contains a source of lipids. This is particularly relevant if the food product of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. The fat source preferably has a ratio of n-6 to n-3 fatty acids of about 5:1 to about 15:1; for example about 8:1 to about 10:1.

The food product of the invention also contains preferably all vitamins and minerals understood to be essential in the daily diet and in nutritionally significant amounts. Minimum requirements have been established for certain vitamins and minerals. Examples of minerals, vitamins and other nutrients optionally present in the food product of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorus, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the food product of the invention may contain emulsifiers and stabilizers such as soy, lecithin, citric acid esters of mono- and di-glycerides, and the like.

The food product of the invention may also contain other substances which may have a beneficial effect such as lactoferrin, nucleotides, nucleosides, and the like.

The food product according to the invention is preferably a synthetic nutritional composition. In this case, it can be a starter infant formula, an infant formula, a baby food, an infant cereal composition, a follow-on formula or a growing-up milk, and the food product is preferably a starter infant formula.

The food product of the invention can further comprise at least one probiotic bacterial strain, the probiotic bacterial strain preferably being *Bifidobacteria* and/or *Lactobacilli*. The food product is particularly advantageous for the enhancement of the oral tolerance to allergens.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus reuteri* sold by BioGaia A.B under the trademark *Reuteri*, *Lactobacillus johnsonii* CNCM 1-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The food product of the invention can further comprise at least one prebiotic, usually in an amount between 0.3 and 10% by weight of food product.

For example the food product can also comprise prebiotics other than the N-acetyl-lactosamine, the sialylated oligosaccharide, and the fucosylated oligosaccharide according to the invention. Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such as fructooligosaccharides (FOS) and galactooligosaccharides (GOS). A combination of prebiotics may be used such as 90% GOS with 10% short chain fructo-oligosaccharides such as in the product by BENEO-Orafti sold under the trademark Orafti® oligofructose (previously Raftilose®) or 10% inulin such as in the product sold by BENEO-Orafti under the trademark Orafti® inulin (previously Raftiline®). A particularly preferred combination of prebiotics is 70% short chain fructo-oligosaccharides and 30% inulin, which is a product sold by BENEO-Orafti under the trademark "Prebio 1".

According to preferred embodiment of the invention, the food product according to the invention is preferably, for use in preventing and reducing the risk and/or reducing the severity and/or reducing the occurrence of food allergies and related food allergy effects on health. The effects are preferably (i) skin effects, atopic dermatitis, rash, or redness; (ii) effects on the immune system or inflammation status; or (iii) effects on the gastro-intestinal system such as colics, abdominal pain and the like.

The composition according to the invention can further comprise other nutritional compounds that synergize with the claimed oligosaccharides to deliver the claimed benefits on skin, such as skin allergies or atopic dermatitis. Such additional compounds can be for example specific non-hydrolyzed proteins, low allergenic proteins (i.e. hydrolyzed or partly hydrolyzed proteins), low lactose ingredients, low lactose saccharides or hydrolyzed saccharides. It is postulated that the synergy of the ingredients may be established by the fact that the ingredients all together help to maintain a low physiological level of an effector that stays below threshold where skin effects (such as atopic dermatitis) starts to show.

According to another embodiment of the invention, the food product according to the invention is for use in the enhancement of the oral tolerance to allergens.

The invention is also related to the use of a food product comprising an oligosaccharide mixture comprising of at least one N-acetyl-lactosamine, at least one sialylated oligosaccharide, and least one fucosylated oligosaccharide, as a synthetic nutritional composition (i.e. as a synthetic nutritional agent), for preventing and reducing the risk and/or reducing the severity and/or reducing the occurrence of food allergies and related food allergy effects on health.

The invention is also related to the use of a food product comprising an oligosaccharide mixture comprising at least one N-acetyl-lactosamine, at least at least on sialylated oligosaccharide, and at least one fucosylated oligosaccharide, as a synthetic nutritional composition (i.e. as a synthetic nutritional agent), for the enhancement of the oral tolerance to allergens.

The uses encompass the fact that the food product is a supplement, preferably provided in the form of unit doses.

According to a preferred embodiment, the food product according to the invention is for use in infants and young children. The compositions and uses as per the present invention are particularly suited for infants and children at risk of allergies, having a family history of allergies, or having already experienced some episodes of allergies (especially respiratory allergies or skin allergies). In one embodiment the composition and uses of the invention apply to teenagers or adults at risk of allergies or having experiences episodes of allergies (especially respiratory allergies or skin allergies). In one embodiment the invention encompasses the use of the claimed composition in a population of infants or young children and for alleviating the symptoms of allergies or reducing the risk of allergies later in life.

The food product may be prepared in any suitable manner known in the art according to the type of product, and the oligosaccharide mixture of the invention may be added to the product at an appropriate stage during the manufacturing process. For example, an infant formula may be prepared by blending together the protein source, together with any carbohydrates other than lactose, and the fat source in appropriate proportions. Emulsifiers may be added if desired. Vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenized, for example in two stages between about 10 MPa and about 30 MPa in the first stage and between about 2 MPa and about 10 MPa in the second stage. The homogenized mixture may then be further cooled to add any heat sensitive components, such as vitamins and minerals. The pH and solids content of the homogenized mixture are conveniently adjusted at this point.

The homogenized mixture is transferred to a suitable drying apparatus such as a spray dryer or freeze dryer and converted to powder. The powder should have a moisture content of less than about 5% by weight. The N-acetyl-lactosamine, sialylated oligosaccharide(s) and fucosylated oligosaccharide(s) may be added at this stage by dry-mixing along with the probiotic bacterial strain(s) if used, or by blending them in a syrup form of crystals, along with the probiotic bacterial strain(s) if used, and spray-dry (or freeze-dry).

The oligosaccharide mixture of the invention is preferably added directly to infant formula by dry mixing. However, if it has been prepared from an animal milk, for example as described below, it may be convenient to add the oligosaccharide mixture without first removing all the lactose. As an infant formula contains a carbohydrate component which is often wholly or partially constituted by lactose, it will be apparent to the person skilled in the art that the amount of carbohydrate in the infant formula will need to be adjusted to take into account the additional carbohydrate that will be provided by the added oligosaccharide mixture. The final concentration of the oligosaccharide mixture in the young child or infant food product or formula is preferably from 0.3 to 4%, preferably from 0.75 to 1.54% by weight of dry matter. This corresponds to a concentration of from 0.2 to 5 grams per liter of reconstituted formula, preferably from 1 to 2 g/l. However, these amounts should not be construed as limitative and should be adapted to the target population, for example based on the weight and age or health of the young child or infant. Preferably, the formula or feed containing the oligosaccharide mixture of the invention is given to the infant each time it is fed.

Alternatively, the oligosaccharide mixtures may be added to wet infant or adult food products by wet mixing. The mixture may be added to the infant formula at concentrations of from about 0.2 to about 5 grams of oligosaccharides per liter of product. However, these amounts should not be construed as limitative and should be adapted to the target population, for example based on the weight and age of the young child or infant, or the health of the specific population. When wet mixing is used, the oligosaccharide blend is preferably added in the form of syrup. The syrup may contain up to 80% total solids, but this should not be limitative.

Although it is preferred to supplement food products specifically targeted towards infant nutrition, it may be beneficial to supplement food products, which are not specifically targeted, or are targeted at the adult population. For example, the oligosaccharide mixtures of the invention can be incorporated into healthcare nutrition products and nutritional products for the elderly. Such food products may include milk, yoghurt, curd, cheese, ice cream, among others. Such food products include also oral food supplement, and enteral nutrition preparations or example for tube feeding administration.

In addition to the oligosaccharide mixture of the invention, a food product such as an infant formula may comprise one or more further oligosaccharides which are added separately.

The invention will now be illustrated by reference to the following examples.

Example 1

An example of an infant formula containing an oligosaccharide mixture according to the present invention is given below. Another example is based on commercial NAN and/or Lactogen Infant formulae (from Nestle, Switzerland) to which the specific oligosaccharides of the invention are added as in the amount stated below.

| Nutrient | per 100 kcal | per liter |
| --- | --- | --- |
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |

-continued

| Nutrient | per 100 kcal | per liter |
|---|---|---|
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| 3' sialyllactose (mg) | 30 | 200 |
| 6' sialyllactose (mg) | 6 | 40 |
| LNnT (mg) | 30 | 200 |
| 2FL (g) | 0.3 | 2.0 |

Experimental Data

Finding Summary

The findings outlined below show that a specific blend of oligosaccharides promotes the metabolic activity and growth of lactic acid bacteria, such as *Bifidobacterium longum* subsp *infantis*. Without wishing to be bound by theory, this effect might in part explain the observation that relatively low amounts of such specific oligosaccharide blends were found in early milk of mothers, whose cesarean born children developed atopic allergies and especially atopic eczema up to the age of 2 years. This indicates that, according to the invention, providing a nutritional composition with a secured level of the specific oligosaccharides blend together with hydrolyzed proteins (fully, extensively or partially) may help reestablishing the natural balance of bacteria in the intestinal tract of infants and/or thus positively influence the health status in regards to the prevention and/or treatment of skin conditions and skin diseases, preferably atopic dermatitis. Further by providing an example of a new and actual health effect of the nutrition composition of the invention, especially as an infant formula, the findings demonstrate the usefulness of the invention.

Study Model 1: Stimulation of *Bifidobacterium longum* Subsp *Infantis*

Approach:

*Bifidobacterium longum* subsp *infantis* (ATCC15697) was grown anaerobic in API growth medium supplemented either with 1% (w/v) glucose, or 1% (w/v) 2'fucosyllactose (2FL) or 1% (w/v) lacto-N-neotetraose (LNnT) or 1% (w/v) 6'sialyllactose (6SL) or 1% (w/v) of a combination of equal amounts of 2FL, LNnT and 6SL. Each overnight culture was diluted to have a starting OD600 of 0.1 in DMEM (Dulbeccos modified Eagle Medium) containing as a carbon source 0.1% glucose. This medium was used without any further carbohydrate supplement or with additional 1% (w/v) glucose, or 1% (w/v) 2'fucosyllactose (2FL) or 1% (w/v) lacto-N-neotetraose (LNnT) or 1% (w/v) 6'sialyllactose (6SL) or 1% (w/v) of a combination of equal amounts of 2FL, LNnT and 6SL. Conditioning of DMEM media was thus done at 37° C. anaerobic.

After another over night incubation, growth of bacteria was monitored by measuring OD at 600 nm. Conditioned media were then centrifuged and supernatants filtered through a 0.22 micrometer filter to remove bacteria. Acetate in conditioned media was quantified by HPLC using a Hi-Plex H column and a UV detector.

Figure 1:
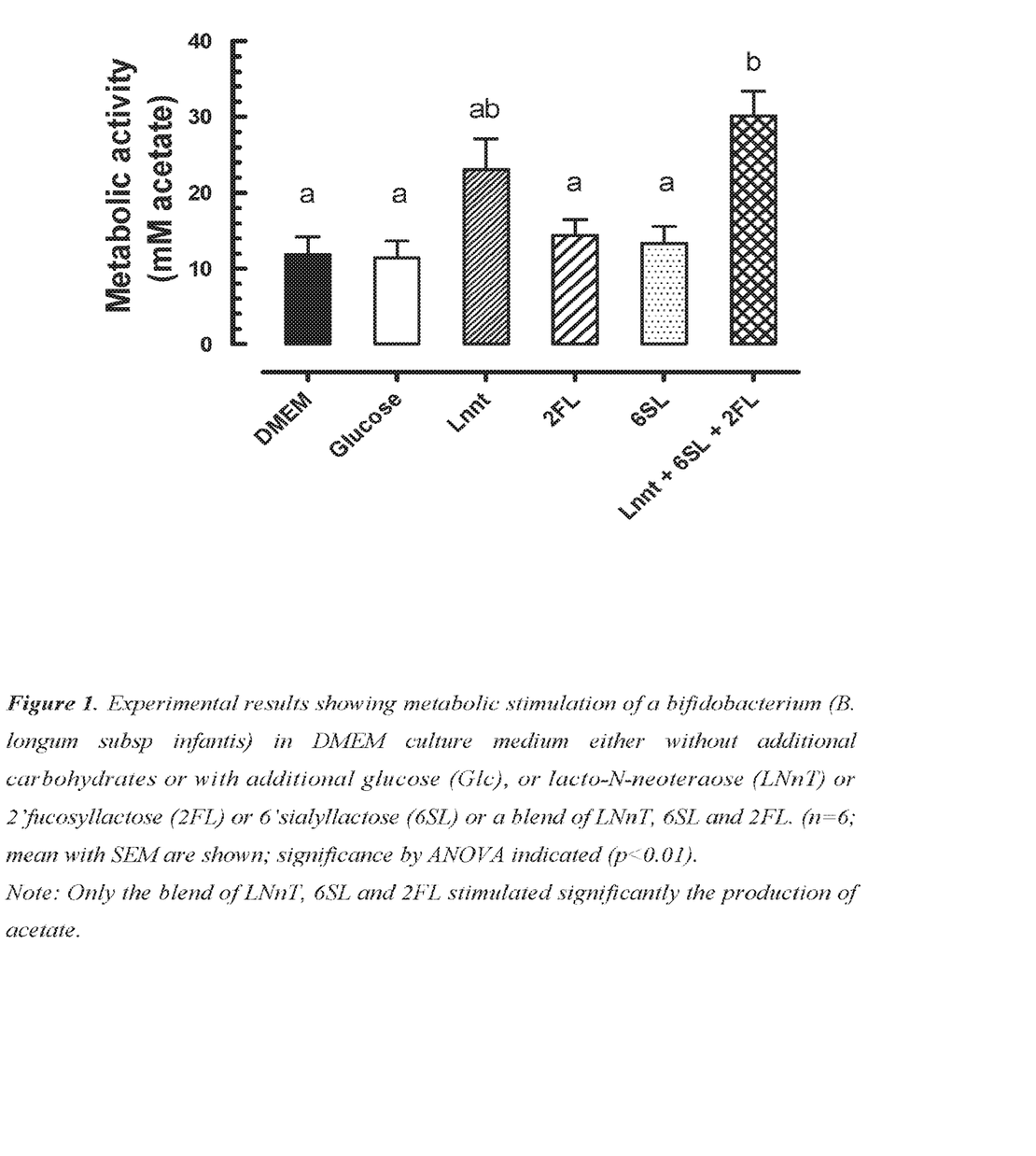
FIG. 1 illustrates experimental results indicating a metabolic stimulation of a *bifidobacterium* (*B. longum* subsp *infantis*) in DMEM culture medium either without additional carbohydrates or with additional glucose (Glc), or lacto-N-neotetraose (LNnT) or 2'fucosyllactose (2FL) or 6'sialyllactose (6SL) or a blend of LNnT, 6SL and 2FL. (n=6; mean with SEM are shown; significance by ANOVA indicated (p<0.01). Note: Only the blend of LNnT, 6SL and 2FL stimulated significantly the production of acetate.

Results:

We surprisingly found that an oligosaccharide blend composed of equal parts of a fucosylated oligosaccharide (e.g. 2'FL), an N-acetylated oligosaccharide (e.g. LNnT) and a sialylated oligosaccharide (e.g. 6SL) significantly increased metabolic activity of a lactic acid bacterium (e.g. *bifidobacterium*), as seen by the formation of acetate (FIG. 1).

Figure 2:
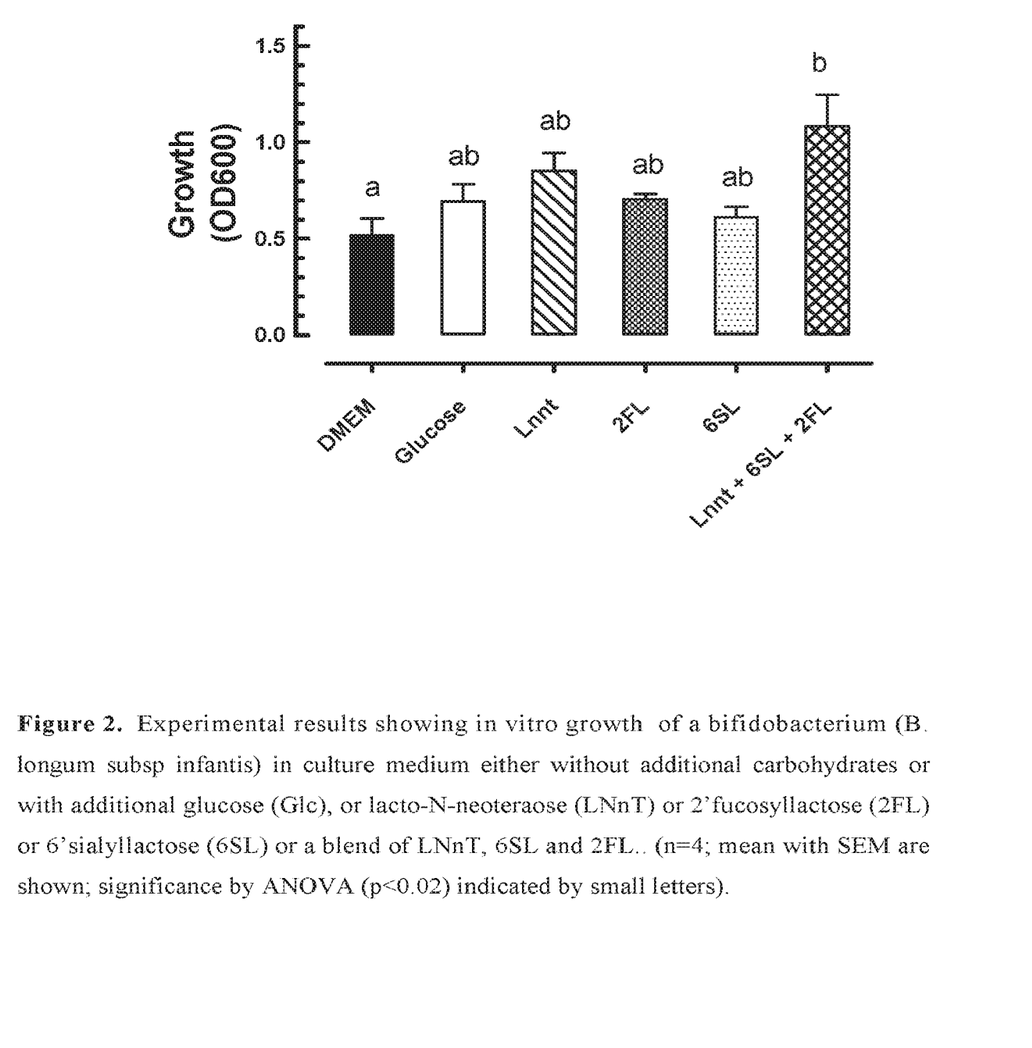
FIG. 2 illustrates experimental results showing in vitro growth of a *bifidobacterium* (*B. longum* subsp *infantis*) in culture medium either without additional carbohydrates or with additional glucose (Glc), or lacto-N-neotetraose (LNnT) or 2'fucosyllactose (2FL) or 6'sialyllactose (6SL) or a blend of LNnT, 6SL and 2FL. (n=4; mean with SEM are shown; significance by ANOVA (p<0.02) indicated by small letters).

The oligosaccharide blend also stimulated growth of the bacterium (FIG. 2).

Study Model 2: Retrospective Epidemiologic Analysis of Breast Milk Samples and Occurrence of Allergic Diseases Up to the Age of 2 Years Approach:

From a cohort of about 52 cesarean born infant mother pairs we analyzed early milk samples for amounts of specific oligosaccharides present. To this end defatted milk samples were diluted 10 to 100 times in water and analyzed by HPAEC (Dionex) equipped with a CarboPac PA1 column (Dionex) and an electrochemical detector. Oligosaccharide identification and quantification was done with authentic oligosaccharide standards. We plotted absence or presence of (A) allergic diseases, (B) atopic allergies, (C) atopic eczema for infants against amounts of an oligosaccharide blend composed of 2FL, LNnT, and 6SL (FIG. 3) or composed of 2FL, LNnT, LNT (lacto-N-tetraose), 6SL and 3SL (3' sialyllactose) (FIG. 4).

Figure 3:
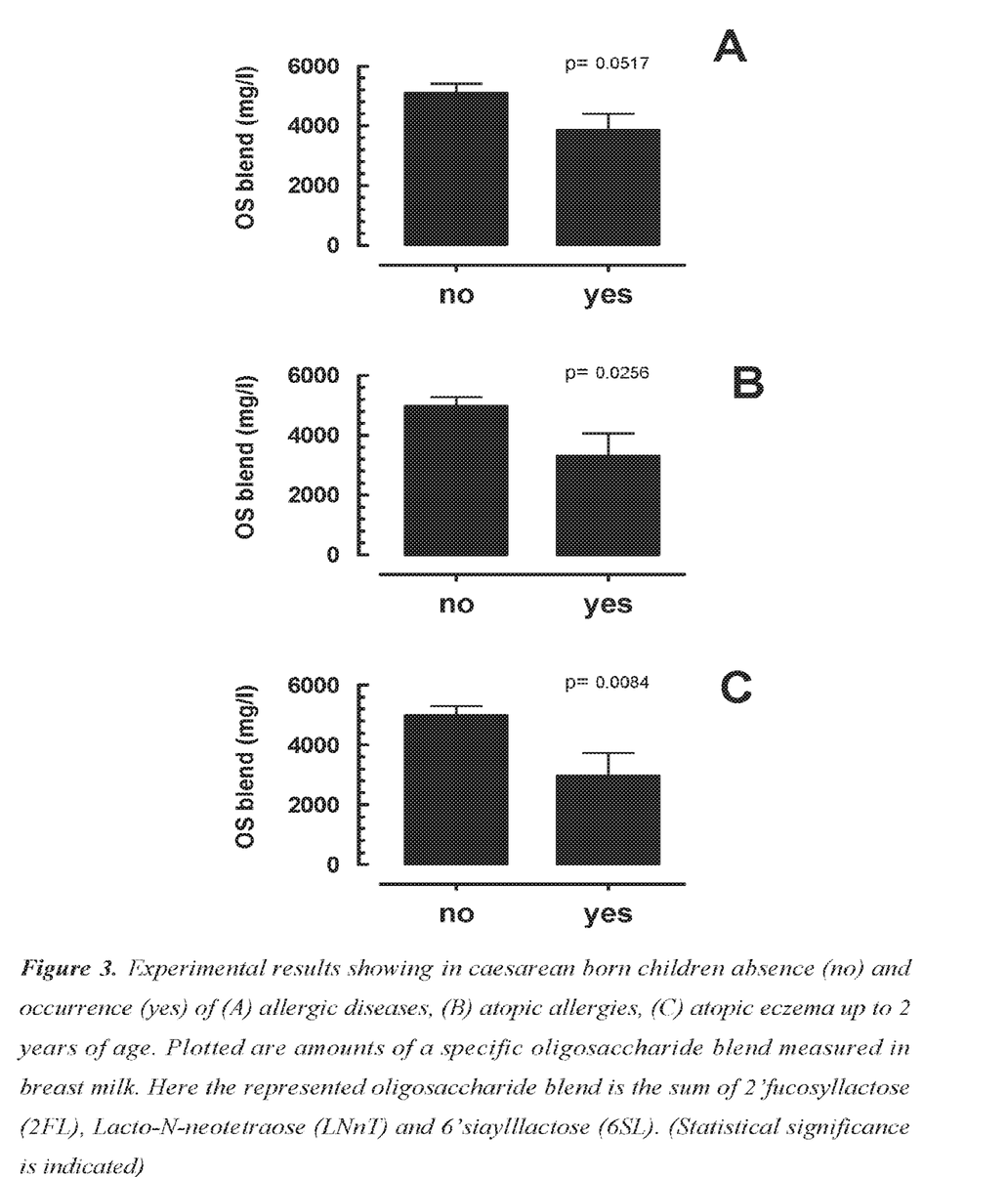
FIG. 3 illustrates experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk. Here the represented oligosaccharide blend is the sum of 2'fucosyllactose (2FL), Lacto-N-neotetraose (LNnT) and 6'sialyllactose (6SL). (Statistical significance is indicated)
Figure 4:
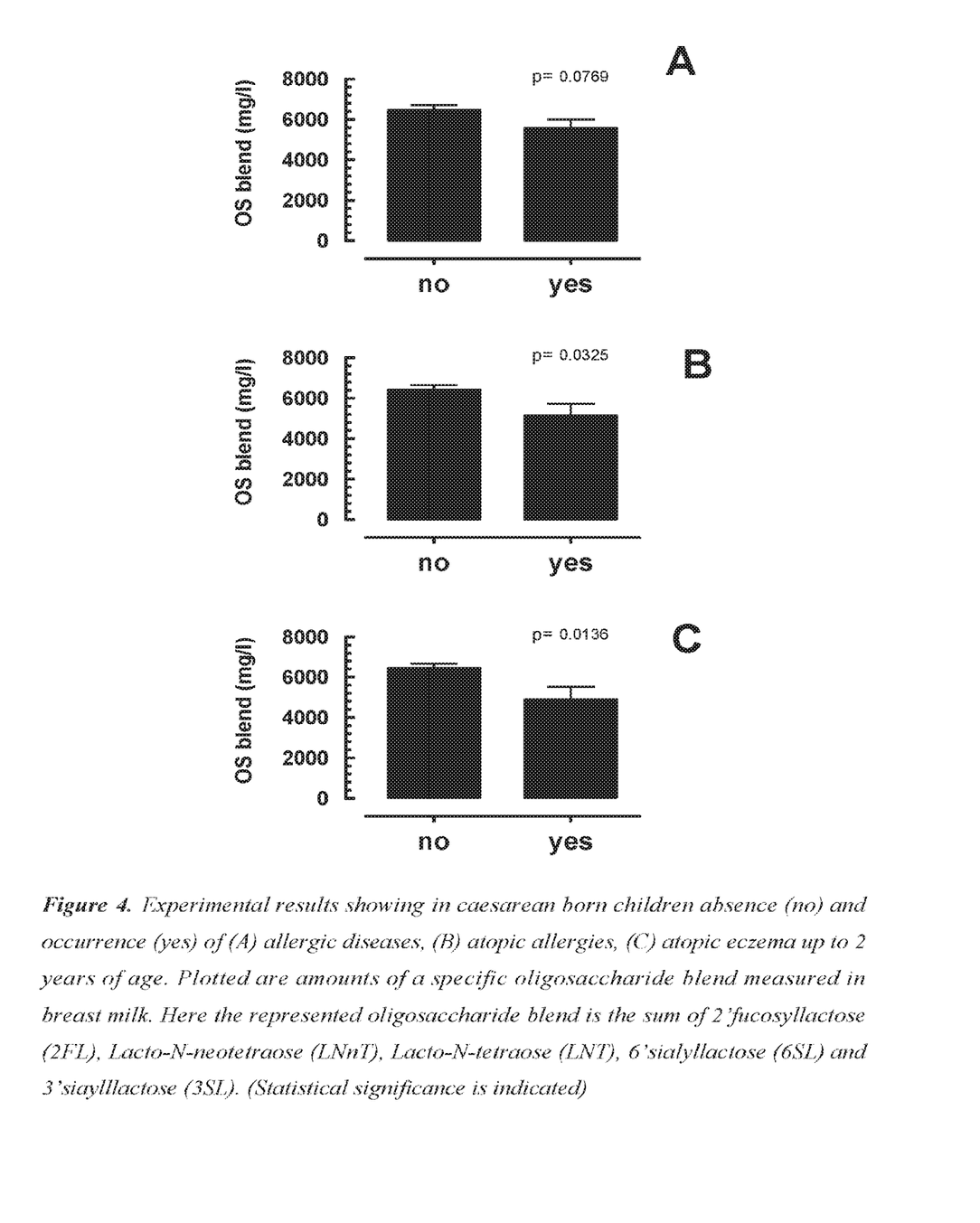
FIG. 4 illustrates the experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk. Here the represented oligosaccharide blend is the sum of 2'fucosyllactose (2FL), Lacto-N-neotetraose (LNnT), Lacto-N-tetraose (LNT), 6'sialyllactose (6SL) and 3' sialyllactose (3SL). (Statistical significance is indicated)

Results:

We surprisingly found a trend to relatively low levels of specific oligosaccharide blends in early milk when children developed an allergic disease (FIG. 3A, 4A). For atopic diseases and especially atopic eczema we measured significantly lower levels of the oligosaccharide blends in early milk of mothers whose children developed such allergies until the age of 2 years.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A food product comprising:
an oligosaccharide mixture at a concentration ranging from about 0.2 to about 5 grams/L, the oligosaccharide mixture consisting of equal parts of lacto-N-neotetraose, 6'-sialyllactose, and 2'-fucosyllactose.

2. The food product of claim 1 further comprising a protein source, a fat source and a carbohydrate source.

3. The food product of claim 1, which is selected from the group consisting of a starter infant formula, an infant formula, a baby food, an infant cereal composition, a follow-up formula and a growing-up milk.

4. The food product of claim 1 further comprising at least one probiotic bacterial strain.

5. The food product of claim 1 further comprising *Bifidobacterium longum* and hydrolyzed proteins.

6. The food product of claim 1 further comprising a fat source that has a ratio of n-6 to n-3 fatty acids of about 8:1 to 10:1.

7. The food product of claim 1, for use in the enhancement of the oral tolerance to allergens.

* * * * *